United States Patent
Lacoste

(10) Patent No.: US 10,420,961 B2
(45) Date of Patent: Sep. 24, 2019

(54) METHOD FOR OPERATING A DEVICE FOR TREATMENT OF A TISSUE AND DEVICE FOR TREATMENT OF A TISSUE

(71) Applicant: THERACLION SA, Malakoff (FR)

(72) Inventor: Francois Lacoste, Gentilly (FR)

(73) Assignee: Theraclion SA, Malakoff (FR)

( * ) Notice: Subject to any disclaimer, the term of this patent is extended or adjusted under 35 U.S.C. 154(b) by 207 days.

(21) Appl. No.: 15/106,888

(22) PCT Filed: Dec. 11, 2014

(86) PCT No.: PCT/EP2014/077448
§ 371 (c)(1),
(2) Date: Jun. 21, 2016

(87) PCT Pub. No.: WO2015/096995
PCT Pub. Date: Jul. 2, 2015

(65) Prior Publication Data
US 2017/0001042 A1    Jan. 5, 2017

(30) Foreign Application Priority Data
Dec. 23, 2013    (EP) .................................... 13199288

(51) Int. Cl.
*A61N 7/00*    (2006.01)
*A61N 7/02*    (2006.01)
(Continued)

(52) U.S. Cl.
CPC .............. *A61N 7/00* (2013.01); *A61N 7/02* (2013.01); *A61B 2017/008* (2013.01);
(Continued)

(58) Field of Classification Search
CPC .... A61N 7/00; A61N 7/02; A61N 2007/0065; A61N 2007/0082; A61N 2007/0078;
(Continued)

(56) References Cited

U.S. PATENT DOCUMENTS

| 6,106,464 A * | 8/2000 | Bass ....................... A61B 8/00 600/439 |
| 6,325,769 B1 * | 12/2001 | Klopotek ................. A61N 7/00 601/2 |

(Continued)

FOREIGN PATENT DOCUMENTS

| EP | 2 332 614 A1 | 6/2011 |
| WO | 2011/069985 A1 | 6/2011 |

OTHER PUBLICATIONS

International Search Report Corresponding to PCT/EP2014/077448 dated Apr. 20, 2015.
(Continued)

*Primary Examiner* — Sanjay Cattungal
(74) *Attorney, Agent, or Firm* — Michael J. Bujold

(57) ABSTRACT

A method of operating a device (1) for treatment of a tissue (6) of a living being and such a device (1) including a transducer (2) comprising at least two subtransducers (2', 2"), each for emitting a sub-beam (8") of ultrasound waves, preferably high intensity focused ultrasound waves, for irradiating the tissue (6). Each of the sub-beams (8") is focused on or focusable onto a focal point (F). In order to reduce skin burns, the intersection Area ($A_{si}$) of a skin surface (7) for each sub-beam (8") is evaluated and a power ($P_{si}$) and/or a duration ($t_{si}$) of the irradiation, for every sub-transducer (2', 2"), is determined as a rate of the total power ($P_{total}$) or duration ($t_{total}$) depending from the evaluated intersection area ($A_{si}$).

15 Claims, 4 Drawing Sheets

Figure 1:
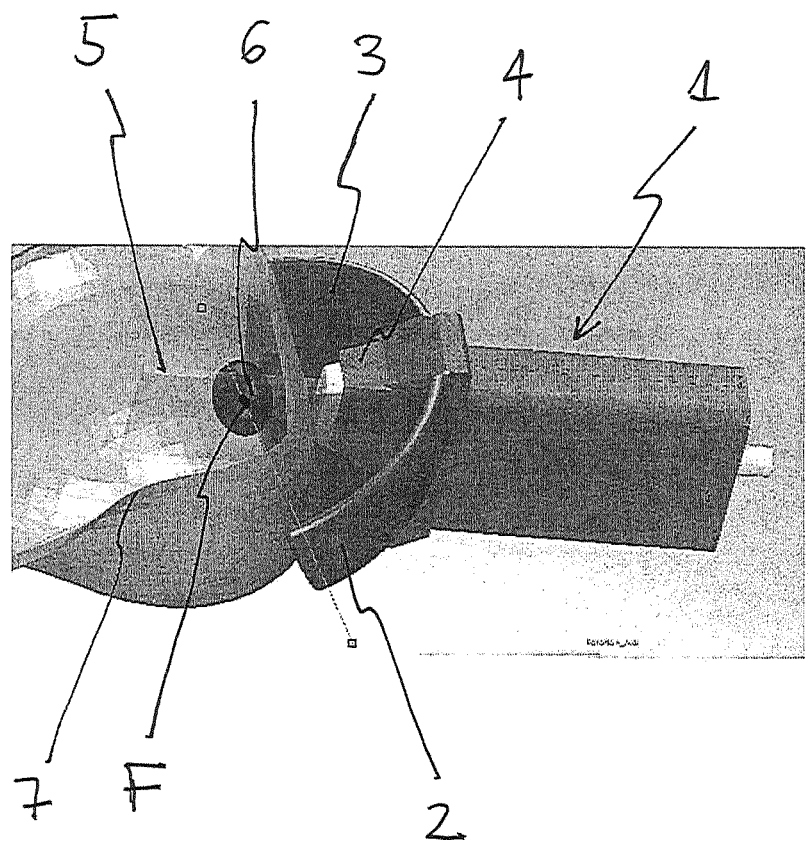

(51) Int. Cl.
*A61B 17/00* (2006.01)
*A61B 90/00* (2016.01)

(52) U.S. Cl.
CPC ........... *A61B 2017/00106* (2013.01); *A61B 2017/00132* (2013.01); *A61B 2090/061* (2016.02); *A61N 2007/0065* (2013.01); *A61N 2007/0078* (2013.01); *A61N 2007/0082* (2013.01)

(58) Field of Classification Search
CPC ........ A61B 2090/061; A61B 2017/008; A61B 2017/00132; A61B 2017/00106
USPC .................................................. 600/437–469
See application file for complete search history.

(56) References Cited

U.S. PATENT DOCUMENTS

| | | | |
|---|---|---|---|
| 8,409,099 B2 | 4/2013 | Vitek et al. | |
| 2004/0162507 A1* | 8/2004 | Govari | A61N 7/02 601/2 |
| 2006/0058678 A1* | 3/2006 | Vitek | A61B 8/4281 600/459 |
| 2006/0241527 A1* | 10/2006 | Muratore | A61B 8/08 601/2 |
| 2008/0194955 A1* | 8/2008 | Lacoste | A61N 7/02 600/439 |
| 2009/0312693 A1 | 12/2009 | Thapliyal et al. | |
| 2010/0094178 A1* | 4/2010 | Lacoste | A61N 7/02 601/2 |
| 2010/0274161 A1* | 10/2010 | Azhari | A61N 7/02 601/4 |
| 2011/0319765 A1* | 12/2011 | Gertner | A61N 7/02 600/453 |
| 2012/0065494 A1* | 3/2012 | Gertner | A61B 5/055 600/411 |
| 2012/0209150 A1 | 8/2012 | Zeng et al. | |
| 2013/0023862 A1* | 1/2013 | Marrouche | A61N 7/02 606/3 |
| 2013/0053691 A1* | 2/2013 | Kawabata | A61B 8/08 600/431 |
| 2015/0025420 A1* | 1/2015 | Slayton | A61N 7/00 601/2 |
| 2015/0157383 A1* | 6/2015 | Chao | A61N 7/02 606/27 |
| 2016/0008634 A1* | 1/2016 | Payne | A61B 8/4227 600/411 |

OTHER PUBLICATIONS

Written Opinion Corresponding to PCT/EP2014/077448 dated Apr. 20, 2015.

* cited by examiner

METHOD FOR OPERATING A DEVICE FOR TREATMENT OF A TISSUE AND DEVICE FOR TREATMENT OF A TISSUE

The invention relates to a method for operating a device for treatment of a tissue of a living being and to such a device in accordance with the preamble of the independent claims.

The device includes a transducer comprising at least two sub-transducers, each for emitting a sub-beam of ultrasound waves, preferably high intensity focused ultrasound waves. The waves are used for irradiating the tissue, each of the sub-beams being focused on or focusable onto a focal point.

Ultrasound waves, in particular high intensity focused ultrasound (HIFU) are mainly used for treatment of tumours of breast, thyroid, prostate and uterus. High intensity ultrasound waves are focused onto a focal point located within the tumour to be treated. During irradiation, heat is created when the acoustic waves are absorbed by the tissue. The temperature can rise up to 85° C., whereby the tissue is destroyed by coagulation necrosis. One big advantage of a treatment with HIFU is that it is non-invasive, thereby considerably reducing risks for the patient.

A known problem with HIFU is however, that the acoustic waves are not only absorbed by the tissue to be treated, but also by the surrounding tissue, including the skin. In order to avoid skin burns, cooling of the skin is used, as exemplary described in WO 2011/069985 A1.

Another approach is to lower the intensity of the acoustic wave at the skin while maintaining enough power at a given depth. This can be done by using wide aperture systems as exemplary described in U.S. Pat. No. 8,409,099 B2.

HIFU systems, however, have a small focus point. The entire tissue must therefore be treated by scanning the focal point over the entire tissue with known methods. Even when using high aperture system, the skin is still exposed to a high burn risk. This because depending on the orientation of the treatment head and the position of the living being, the tissue to be treated or part of it may be very shallow. Therefore, the beam cuts the skin surface over a surface which can vary depending on the above cited factors. If the power of the ultrasound beam emitted by the transducer is uniform throughout the whole transducer, the beam intensity at the skin surface and thus the skin heat stress will vary strongly.

It is therefore an object of the present invention to provide a method for operating a device for treatment of tissue of a living being and a device for treatment of a tissue of a living being which solve the problems of the prior art and in particular can reduce and possibly avoid a skin damage when treating a tissue.

This problem is solved by a method according to the characterizing portion of the independent claims.

According to the present invention, for performing a method for operating a device for treatment of a tissue of a living being, a device including a transducer comprising at least two sub-transducers is provided. Each sub-transducer is used for emitting a sub-beam of ultrasound waves, preferably high intensity focused ultrasound waves. The waves are used for irradiating the tissue, each of the sub-beams being focused on or focusable onto a focal point.

The method further includes the step of positioning the transducer such that at least one focal point of a sub-beam is located within the tissue to be treated;

Preferably all the focal points of the sub-beams are located within the tissue to be treated, and even more preferably all the focal points of each sub-beam are focused onto a single focal point.

Further, the total power ($P_{total}$) and duration ($t_{total}$) of the irradiation to be delivered to the tissue is defined. Defining can be done either manually by entering the desired values with a user interface by an operator or automatically by the device itself. In particular, if the device is equipped with imaging means which can determine size and other parameters of the tissue to be treated, it is possible that a control means of the device can define the total power ($P_{total}$) and duration ($t_{total}$) of irradiation accordingly.

Each intersection area ($A_{si}$) of a skin surface with a corresponding sub-beam of a sub-transducer is then evaluated, i.e. determined. This can be done by extrapolating data from a three-dimensional model of the irradiated area or by other methods as shown below.

According to the present invention, "skin" is meant to be the first tissue intersected by a beam when irradiating. This tissue is, as a rule, not the tissue to be treated. In the case of endocavitary systems such as the ones used for the treating of prostate tumours which are inserted rectally, the first tissue intersected by the beam is a mucosa, which in this case is at risk. Therefore, skin according to the present invention is meant to include also mucosae.

In the above, skin burns are considered. Is must be noted that however, other kind of damage such as mechanical damage caused by cavitation etc. may occur. The invention therefore applies also to other types of damage caused by ultrasonic beams. Further according to the invention, the power ($P_{si}$) and/or duration ($t_{si}$) of the irradiation for every sub-transducer is then determined as a rate of the total power ($P_{total}$) and duration ($t_{total}$), respectively, in dependence from the evaluated intersection area ($A_{si}$). Preferably, the power ($P_{si}$) and/or duration ($t_{si}$) are chosen substantially proportional to the intersection area.

In particular, the power ($P_{si}$) is chosen according to the following equation:

$$P_{si} = P_{total} * \frac{A_{si}}{\sum_{i=1}^{n} A_{si}}$$

Wherein n is the number of the sub-transducers and thus of the sub-beams.

By taking into consideration the intersection area ($A_{si}$) of each sub-beam, the risk of tissue damage of the skin, in particular of burn damage, can be minimized without affecting the total irradiation of the tissue to be treated. In particular, the power ($P_{si}$) and/or duration ($t_{si}$) of sub-beams arranged close to the skin can be reduced compared to sub-beams arranged further away.

As an alternative, the power of each sub-transducer may be kept constant, and the duration of the irradiation, and thus the delivered energy, may be related, in particular proportionally to the intersection area ($A_{si}$) and determined similarly to the power. This has the advantage, that only one ultrasound generator is necessary for all the sub-transducers, whereby only on/off switches must be provided for each sub-transducer.

The intersection area ($A_{si}$) is preferably evaluated taking into consideration the sub-beam area at the sub-transducer surface ($A_{tr}$) and a distance between skin surface and the sub-transducer surface ($D_{ts}$).

This is based on the principle that the intersection area ($A_{si}$) is related to the distance between skin surface and the sub-transducer surface ($D_{ts}$).

In particular when a transducer with a fixed focal point and with a surface which substantially corresponds to a sector or area of a sphere surface is used, the distance between the sub-transducer and the focal point ($D_{tf}$) is equal to the radius of the sphere. The area of the sub-transducer surface ($A_{tr}$) is also a known parameter.

Alternatively transducers which are focusable, i.e. by phase array technique, may be used.

Preferably the intersection area ($A_{si}$) is evaluated according to the following equation:

$$A_{si} = A_{tr} * \left(\frac{D_{sf}}{D_{tf}}\right)^2$$

wherein $D_{sf}$ is the distance between skin and focal point, which can be calculated as a difference between $D_{tf}$ and $D_{ts}$.

Preferably, the distance between the skin surface and the sub-transducer surface ($D_{ts}$) is determined by means of A-mode echography. Accordingly, an A-mode echography imaging device may be integrated into the transducer or located adjacent to the transducer in order to determine the distance between the skin surface and the sub-transducer surface ($D_{ts}$).

Preferably, every sub-transducer may be equipped with means for determining the distance between the skin surface and the sub-transducer surface ($D_{ts}$). The means for determining the distance are not only limited to A-mode echography but can include, as cited above, means for determining a three-dimensional model of the irradiated area or other means such as laser distance measuring means or the like.

If the intersection area ($A_{si}$) is below a given value, the power ($P_{si}$) and/or the duration ($t_{si}$) of the corresponding sub-transducer, depending on the method used, can be preferably set to zero. Therefore, if the intersection area ($A_{si}$) is subject to an intense irradiation, the corresponding sub-transducer is not operated.

The given value may be defined by an operator or be calculated depending on the total power ($P_{total}$) and/or duration ($t_{total}$) of the irradiation to be delivered to the tissue. Other factors may be taken into account, like the shape of the tissue to be treated, the distance between the tissue to be treated and the skin surface, the type of tissue to be treated, the type of tissue(s) surrounding the tissue to be treated and the location of the tissue to be treated etc.

Alternatively, the sub-transducers to be used may be chosen taking into account the location of the tissue to be treated.

Preferably, the method further comprises the step of triggering every sub-transducer to emit a sub-beam of ultrasound waves in order to treat the tissue. This may be done simultaneously or preferably sequentially, meaning that the sub-transducers are triggered one after another.

The invention further relates to a device for treatment of a tissue of a living being, which is preferably operated with a method according to the present invention. For advantages and further preferred embodiments, reference is made to the method cited above.

The device includes a transducer comprising at least two sub-transducers, each for emitting a sub-beam of ultrasound waves, preferably high intensity focused ultrasound waves, for irradiating the tissue, each of the sub-beams being focused on or focusable onto a focal point.

The device further includes means for determining an intersection area ($A_{si}$) of a skin surface with each sub-beam and control means for controlling the device, the control means being able to determine, based on a total power ($P_{total}$) and duration ($t_{total}$) of the irradiation to be delivered to the tissue, a power ($P_{si}$) and/or duration ($t_{si}$) of the irradiation for every sub-transducer as a rate of the total power ($P_{total}$) or duration ($t_{total}$) depending, preferably substantially proportionally, from the evaluated intersection area ($A_{si}$). The means for determining and the control means are typically formed by a processor of the device or by a computer controlling the operation of the device.

Preferably, the device has a transducer with a transducer surface which is substantially a sector of a hemispherical surface.

This configuration is preferred because of its focusing properties, in particular if a transducer with a fixed focal point is used, and because it offers good irradiation properties with a wide irradiation angle, depending on the shape of the transducer. Other configurations such as sectors of a cylinder surface or any arbitrary concave surface may also be used.

Further preferred, every sub-transducer has substantially the same sub-transducer surface ($A_{tr}$) and/or sub-transducer shape. This is preferably the case when a method according to the present invention is used, whereby setting the same sub-transducer surface and/or shape for every sub-transducer can substantially simplify the evaluation of the intersection Area ($A_{si}$) and thus reduce calculating effort of the control means.

Preferably, the transducer of the device has eight sub-transducers.

Further preferred, each sub-transducer of the device has a fixed focal point, whereby the focal points of the sub-transducers are preferably coincident.

Another aspect of the invention refers to a method for operating a device for treatment of a tissue of a living being. The device includes at least one transducer for emitting a beam of ultrasound waves, preferably high intensity focused ultrasound waves. The waves are used for irradiating the tissue and the beam is focused on or focusable onto a focal point. The device further includes an imaging device having at least an imaging plane intersecting the focal point.

The method comprises the step of positioning the at least one transducer such that the focal point is located within the tissue to be treated.

Further, the at least one transducer is oriented such that a distance between the focal point and the skin surface intersected by the beam ($A_{total}$) is as constant as possible throughout the whole skin surface, whereby the focal point is not moved. In other words, the at least one transducer is oriented such that the variations of the distance between the focal point and the skin surface are minimal.

As cited above, the distance between the transducer surface and the skin surface may be determined at different locations of the transducer using A-mode echography, a three dimensional model of the irradiation area or the like.

According to the invention, this method applies to devices of the known art with only one transducer as well as to devices with a plurality of sub-transducers as described above. Both aspects of the invention optimize the energy distribution on the skin surface such that skin burns and other damages can be reduced or avoided.

Orienting the at least one transducer is preferably done such that the beam or sub-beams are as perpendicular to the skin as possible. This means that the skin must be as perpendicular as possible to a virtual line drawn between the focal point and the transducer surface, that means orthogonal to the transducer surface.

Alternatively the at least one transducer may be oriented such that the distance between the focal point and the skin is as constant as possible. The distance between the focal point and the skin surface may be determined as described above.

Preferably, in order to orient the transducer, the at least one transducer is rotated around an axis contained in the imaging plane of the ultrasonic imaging device. This is particularly advantageous in order to simplify the construction and the control of a device used with this method, since only one rotational drive is required.

Alternatively or additionally, the at least one transducer may be rotated around an axis perpendicular to the imagine plane which preferably does not cross the focal point of the at least one transducer. Also in this case, a simple device may be used with this method, since in order to perform this rotation, no special drive and control means must be provided.

In a preferred embodiment, the distance between the focal point and the skin surface is determined taking into consideration a three dimensional model of the irradiated area, and thus also of the skin surface, as cited above. This model may be obtained by means of the imaging device.

For advantages and further preferred embodiments of the device according to the present invention, reference is made to the method cited above.

As an alternative, A-mode echography means can be placed at the centre of the at least one transducer surface in order to determine the distance between the transducer surface and the skin surface as cited above.

If the tissue to be treated is large and the focal point must be scanned over the entire tissue to be treated (pulse and pause method), the transducer orientation may be adjusted for each pulse, preferably during the pauses.

Figure 2:
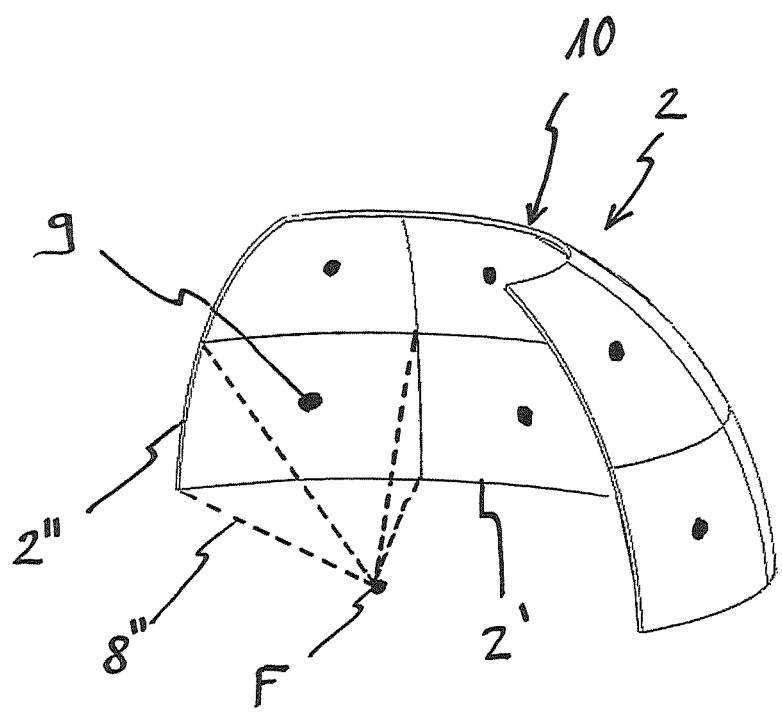
Figure 3:
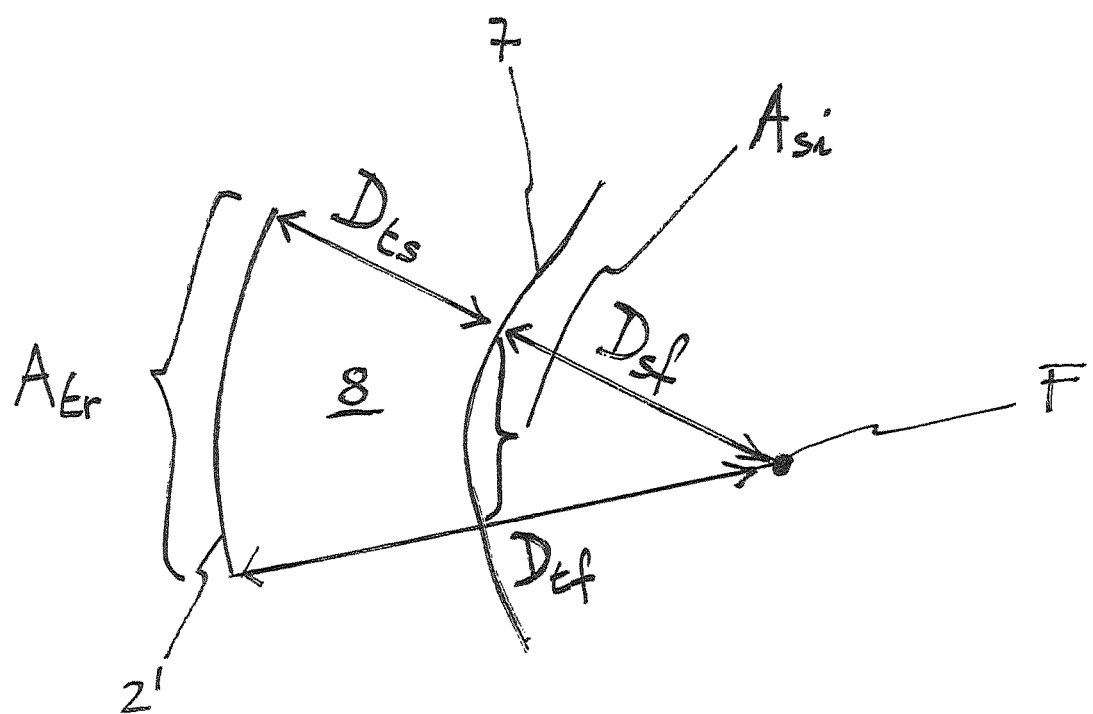
Figure 4:
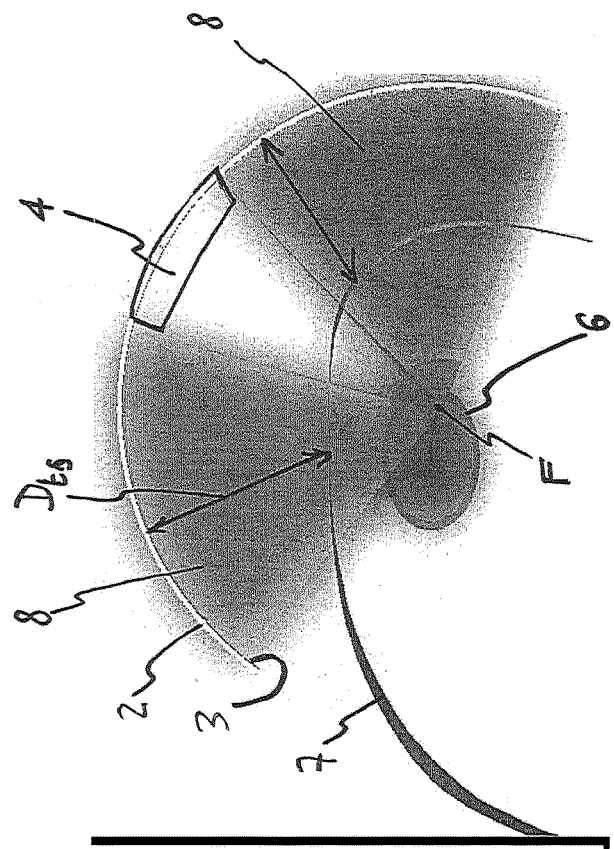
Figure 4:
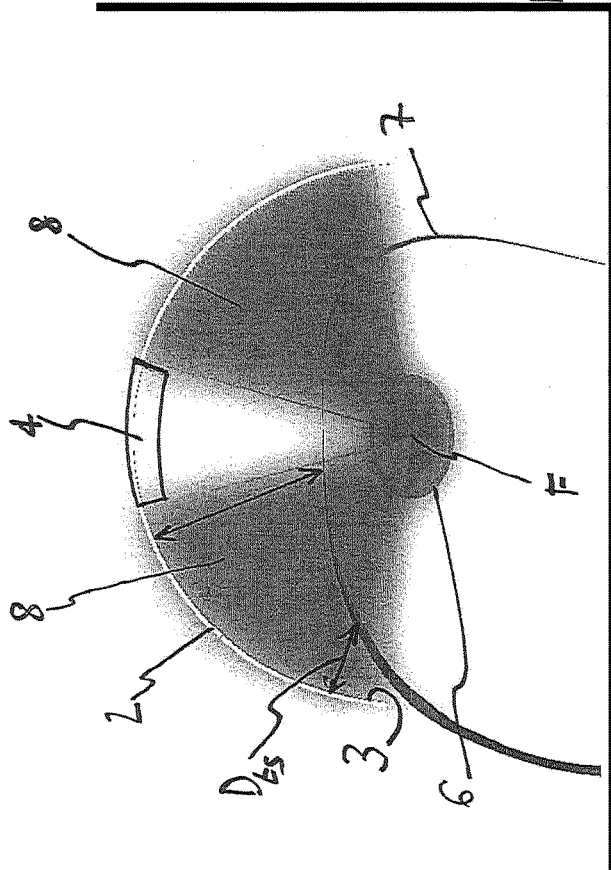

The invention will be now described according to a preferred embodiment of the present invention in connection with the drawings, which show:

FIG. 1: a schematic view of a device according to the present invention;

FIG. 2: a schematic arrangement of the sub-transducers of the device according to FIG. 1;

FIG. 3: a schematic arrangement of a sub-transducer of the device according to FIG. 1; and FIG. 4: a schematic comparison between a method and a device according to the prior art (left) and the present invention (right).

FIG. 1 schematically shows a device 1 comprising a transducer 2 with a fixed focal point divided in eight sub-transducers. In FIG. 2 the arrangement of the sub-transducers is shown schematically, whereby for sake of clarity, only six sub-transducers are shown in total and only two sub-transducers 2' and 2" are provided with reference numerals.

The transducer 2 has a transducer surface 3 which is a sector of a spherical surface, with every sub-transducer having a sub-transducer surface $A_{tr}$ as shown in FIG. 3.

The device 1 further includes an imaging device 4, in this case an A-mode echography device, with an imaging plane 5.

The sub-transducers of the transducer 2 are focused on a common focal point F, which also lies within the imaging plane 5 of the imaging device 4. The distance between the transducer surface and the focal point $D_{tf}$ (which is represented schematically in FIG. 3) is therefore the same for each sub-transducer.

The transducer is arranged such that the focal point F is located within a tissue to be treated, schematically represented by a body 6.

The body 6, which in this case is a breast tumour, is not located superficially but is surrounded by healthy tissue which must not be treated. The breast skin is also schematically represented by the skin surface 7.

Regarding FIG. 2, the surfaces of the sub-transducers are also represented schematically. The converging structure 8", represented schematically by the dashed lines and of which only one is shown for sake of clarity, represents the beam emitted by the respective sub-transducer 2".

Every sub-transducer 2', 2" comprises a distance measuring means, shown schematically by the reference numeral 9, which is placed roughly at the centre of the sub-transducer surface and is used for determining the distance between the sub-transducer surface and the skin surface 7 in order to perform the method according to the present invention.

The imaging device 4 is arranged in a gap 10 between neighbouring sub-transducers represented schematically.

After defining the total power ($P_{total}$) and duration ($t_{total}$) of the irradiation to be delivered to the body 6, the distance between the sub transducer surface and the skin surface 7 $D_{ts}$ is measured by the distance measuring means 9 for every sub-transducer.

An intersection area $A_{si}$ (also shown schematically in FIG. 3) of each sub-beam generated by each sub transducer is then evaluated by control means of the device 1 (not shown) according to:

$$A_{si} = A_{tr} * \left(\frac{D_{sf}}{D_{tf}}\right)^2$$

The area of the sub-transducer surface $A_{tr}$ and the distance between sub-transducer surface and focal point F $D_{tf}$ (which is equal to the radius of the surface of the transducer 2) are known parameters of the device 1. Therefore the distance between the skin surface 7 and the focal point F $D_{sf}$ can also be calculated.

Once every intersection area has been evaluated for every sub-transducer, the control means also determine the power $P_{si}$ of the irradiation for every sub-transducer as a rate of the total power $P_{total}$ proportional to the evaluated intersection area $A_{si}$ according to:

$$P_{si} = P_{total} * \frac{A_{si}}{\sum_{i=1}^{n} A_{si}}$$

The control means are then used to trigger the respective sub-transducers in order to irradiate the tissue to be treated located within the body 6.

After irradiation, the transducer 2 is oriented for treating tissue of the body 6 which has not (or not with the desired power) been treated during the preceding irradiation. The distance between the surface of the sub-transducers and the skin surface 7 is measured again, the intersection area $A_s i$ is evaluated and the power $P_{si}$ is determined as described above. This process is repeated until the whole body 6 has been irradiated and hence treated.

FIG. 4 shows schematically on the left an arrangement according to the prior art, wherein a focal point F of a beam emitted or emittable by a transducer 2 with a transducer surface 3 is focused on a tissue to be treated. The beam intersects a skin surface 7. A distance $D_{ts}$ between the transducer surface 3 and the skin surface 7, which is represented schematically by the double-headed arrows, of which only one is provided with a reference sign for sake of clarity, varies throughout the whole skin surface intersected by the beam.

According to the present invention, the transducer 2 is oriented as shown schematically on the right of FIG. 4, such that the distance $D_{ts}$ between the transducer surface 3 and the skin surface 7 is as constant as possible throughout the whole skin surface.

The invention claimed is:

1. A method of operating a device for ultrasonic treatment of a target tissue of a living being, the device comprising:
    a transducer comprising at least two sub-transducers, each for emitting a sub-beam of ultrasound waves for irradiating the target tissue, and each of the sub-beams being focused on or focusable onto a single focal point within the target tissue;
    wherein the method includes the following steps:
        positioning both of the at least two transducers such that the single focal point of a sub-beam is located within the target tissue to be treated, wherein the target tissue to be treated is not a first tissue intersected by a beam when irradiating;
        defining a total power and a duration of the irradiation to be delivered to the tissue;
        determining an intersection surface area of the first tissue intersected by a beam when irradiating with each sub-beam; and
        determining at least one of the total power and the duration of the irradiation for every sub-transducer as a rate of the total power or duration depending upon the determined intersection surface area for the first tissue intersected by a beam when irradiating;
    wherein the intersection surface area is determined by taking into consideration a sub-beam area at a sub-transducer surface and a distance between the first tissue intersected by a beam when irradiating and the sub-transducer surface; and
    wherein the distance between the first tissue intersected by a beam when irradiating and the sub-transducer surface is determined by ultrasonic imaging.

2. The method according to claim 1, wherein the ultrasonic imaging mode is A-mode echography.

3. The method according to claim 1, wherein if the intersection surface area is below a given value, at least one of the power and the duration of the corresponding sub-transducer is set to zero.

4. The method according to claim 1, wherein after the step of determining at least one of the power and the duration of the irradiation, every sub-transducer is triggered to emit a sub-beam of ultrasound waves.

5. A device for ultrasonic treatment of a target tissue of a living being, the device comprising:
    a transducer comprising at least two sub-transducers, each for emitting a sub-beam of ultrasound waves for irradiating the target tissue, and each of the sub-beams being focused on or focusable onto a single focal point within the target tissue,
    wherein the device further comprises:
        means for determining an intersection surface area of a first tissue intersected by a beam when irradiating with each sub-beam, and
        control means for controlling the device, and the control means being able to determine, based upon a total power and a duration of the irradiation to be delivered to the target tissue, at least one of a power and a duration of the irradiation for every sub-transducer as a rate of the total power or the duration, depending upon the determined intersection surface area of the first tissue intersected by a beam when irradiating;
    wherein the intersection surface area is determined taking into consideration a sub-beam area at a sub-transducer surface and a distance between the first tissue intersected by a beam when irradiating and the sub-transducer surface; and
    wherein the distance between the first tissue intersected by a beam when irradiating and the sub-transducer surface is determined by ultrasonic imaging.

6. The device according to claim 5, wherein the transducer has a transducer surface which is substantially a sector of a hemispherical surface.

7. The device according to claim 5, wherein every sub-transducer has substantially at least one of the same sub-transducer surface and sub-transducer shape.

8. The device according to claim 5, wherein the transducer has 8 sub-transducers.

9. The device according to claim 5, wherein each sub-transducer has a fixed focal point, the focal point of one sub-transducer being coincident with the focal point of the at least one other sub-transducers.

10. The device according to claim 5, wherein every sub-transducer comprises an A-mode echography element for evaluating a distance between the first tissue intersected by a beam when irradiating and the sub-transducer surface.

11. A method of operating a device for ultrasonic treatment of a target tissue of a living being, the device comprising:
    at least one transducer for emitting a beam of ultrasound waves for irradiating the target tissue, and the beam being focused on or focusable onto a single focal point within the target tissue; and
    an imaging device having at least an imaging plane intersecting the focal point;
    wherein the method includes the following step:
        positioning the at least one transducer such that the single focal point is located within the target tissue to be treated;
        orienting the at least one transducer such that the distance between the single focal point and a first tissue intersected by a beam when irradiating is as constant as possible throughout the whole first tissue intersected by a beam when irradiating,
    whereby the single focal point is not moved;
        defining a total power and a duration of the irradiation to be delivered to the tissue;
        determining an intersection surface area of the first tissue intersected by a beam when irradiating with each sub-beam; and
        determining at least one of the total power and the duration of the irradiation for every sub-transducer as a rate of the total power or duration depending upon the determined intersection surface area for the first tissue intersected by a beam when irradiating;
    wherein the intersection surface area is determined taking into consideration a sub-beam area at a sub-transducer surface and a distance between the first tissue intersected by a beam when irradiating and the sub-transducer surface; and
    wherein the distance between the first tissue intersected by a beam when irradiating and the sub-transducer surface is determined by ultrasonic imaging.

12. The method according to claim 11, wherein the at least one transducer is rotated around an axis contained in the imaging plane of the ultrasonic imaging device for orienting.

13. The method according to claim 11, wherein the at least one transducer is rotated around an axis which does not cross the focal point for orienting.

14. The method according to claim 11, wherein a three-dimensional representation of the first tissue intersected by a beam when irradiating, obtained by the imaging device, is taken into consideration for determining the distance between the focal point and the first tissue intersected by a beam when irradiating.

15. A device for ultrasonic treatment of a target tissue of a living being, the device comprising:
   at least one transducer for emitting a beam of ultrasound waves for irradiating the target tissue, and the beam being focused on or focusable onto a single focal point within the target tissue;
   an imaging device having at least an imaging plane intersecting the single focal point;
   wherein the device further comprises:
      means for positioning the at least one transducer such that the single focal point is located within the target tissue to be treated;
      means for orienting the at least one transducer such that a distance between the single focal point and a first tissue intersected by a beam when irradiating is as constant as possible throughout an entire first tissue intersected by a beam when irradiating, whereby the single focal point is not moved;
      means for determining an intersection surface area of the first tissue intersected by a beam when irradiating with each sub-beam, and
      control means for controlling the device, and the control means being able to determine, based upon a total power and a duration of the irradiation to be delivered to the target tissue, at least one of a power and a duration of the irradiation for every sub-transducer as a rate of the total power or the duration, depending upon the determined intersection surface area of the first tissue intersected by a beam when irradiating;
   wherein the intersection surface area is determined taking into consideration a sub-beam area at a sub-transducer surface and a distance between the first tissue intersected by a beam when irradiating and the sub-transducer surface; and
   wherein the distance between the first tissue intersected by a beam when irradiating and the sub-transducer surface is determined by ultrasonic imaging.

* * * * *